United States Patent [19]
Futagawa et al.

[11] Patent Number: 5,624,405
[45] Date of Patent: Apr. 29, 1997

[54] PREFILLED SYRINGE AND SYRINGE TIP ASSEMBLY

[75] Inventors: Hitoshi Futagawa, Kusatsu; Masafumi Aramata, Neyagawa; Yoji Arifuku, Kusatsu; Kenji Himeshima, Sanda, all of Japan

[73] Assignee: Nissho Corporation, Osaka-fu, Japan

[21] Appl. No.: 449,545

[22] Filed: May 24, 1995

[30]   Foreign Application Priority Data

May 27, 1994   [JP]   Japan ..................... 6-137975

[51] Int. Cl.⁶ ..................................... A61M 5/32
[52] U.S. Cl. .................. 604/199; 604/200; 604/263; 604/272; 604/187
[58] Field of Search ..................... 604/200, 274, 604/272, 263, 187, 199

[56]   References Cited

U.S. PATENT DOCUMENTS

| | | |
|---|---|---|
| 2,811,155 | 10/1957 | Dunnican et al. . |
| 5,135,496 | 8/1992 | Vetter et al. ................. 604/111 |
| 5,135,514 | 8/1992 | Kimber ..................... 604/240 |
| 5,447,500 | 9/1995 | Bergstresser et al. ................... 604/198 |

FOREIGN PATENT DOCUMENTS

| | | |
|---|---|---|
| 0397951 | 11/1990 | European Pat. Off. . |
| 0520618 | 12/1992 | European Pat. Off. . |
| 0528120 | 2/1993 | European Pat. Off. . |
| 8800479 | 1/1988 | WIPO . |

*Primary Examiner*—V. Millin
*Assistant Examiner*—Cris L. Rodriguez
*Attorney, Agent, or Firm*—Birch, Stewart, Kolasch & Birch, LLP

[57]   ABSTRACT

A prefilled syringe comprising a syringe body of glass; a sealing member with a through-hole extending in the axial direction of said syringe body; a tip member including a top wall, a skirt portion extending therefrom and a tubular projection passing through said top wall, said tubular projection including an outwardly extending projection and an inwardly extending projection; a covering means for closing the outwardly extending projection of said tip member; and a holding member for holding said covering member along with said tip member in place on the mouth portion of said syringe body, said tip member being liquid-tightly fixed to the mouth portion of the syringe body by said holding member.

20 Claims, 6 Drawing Sheets

PREFILLED SYRINGE AND SYRINGE TIP ASSEMBLY

BACKGROUND OF THE INVENTION

1. Field of the Invention

The present invention relates to a prefilled syringe, i.e., a syringe previously filled with a medical solution and, more particularly, a prefilled syringe made of glass which is easy to manufacture, simple to assemble, and affords a sterile environment for a medical solution before injection.

2. Description of the Prior Art

Figure 10:
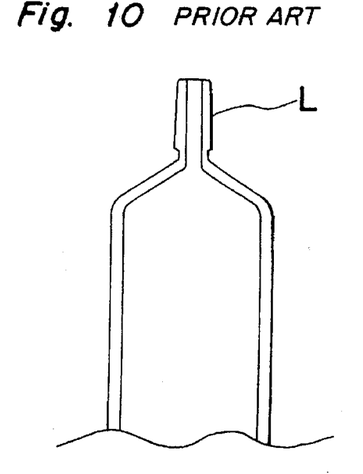
FIGS. 10 to 12 are illustration of structures of prefilled syringes of the prior art.
Figure 11:
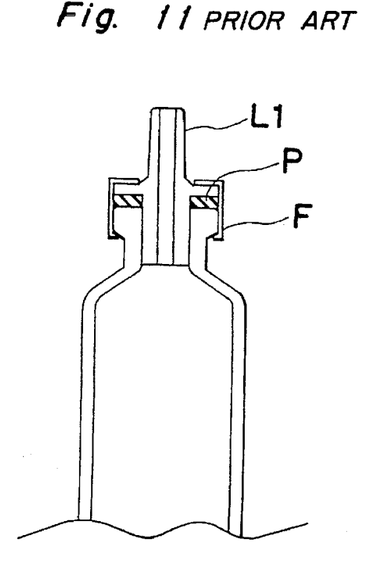
Figure 12:
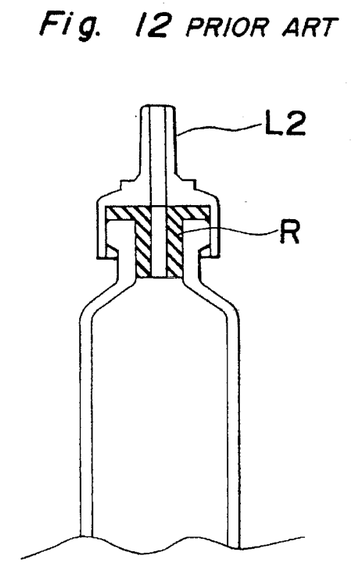

When manufacturing a prefilled syringe with a hollow glass tube, a tip for attachment of a needle is formed into a lure tip, i.e., a reduced hollow tube having a tapering outer wall. Such a lure tip has so far been produced as an integral part of a syringe body as shown in FIG. 10 or as a separate member as shown in FIGS. 11 and 12. The separate lure tip member L1 shown in FIG. 11 is molded out of a synthetic resin, fitted in a narrow mouth of a syringe body through a packing P, and then fixed thereto with an aluminum fitting member F. On the other hand, the separate lure member L2 with a skirt portion as shown in FIG. 12 is molded out of a hard plastic material, and press-fitted on a narrow mouth of a syringe body with a rubber stopper R fitted therein.

However, these prefilled syringes have various problems awaiting a solution. For example, the syringe with the lure tip L as shown in FIG. 10 is low in productivity but high in production cost. Since the lure tip L is produced by thermally softening a glass tube and then shaping it into a certain form, the accuracy thereof is not satisfactory. Thus, the tapering outer wall portion of the lure tip mating with a needle hub or female lure connector has to be polished with whetstones to improve the accuracy. This causes lowering of productivity and an increase in production cost since it is difficult to automate the polishing process of the glass syringes and since it is required to perform a functional test for all the produced glass syringes.

The lure tip for the syringe shown in FIG. 11 must be fixed by an aluminum fitting member, which produces fine powder of aluminum during the fixing process. Thus, the syringe has such disadvantages that there is a fear of contamination of an aseptic room or entering pollution by foreign substances, that foreign matter may enter into the medical solution, and that it requires segregated disposal.

On the other hand, it is a general practice to polish the flange portion of the syringe shown in FIG. 12 to the required outside diameter, as the flanged mouth portion requires finishing of high accuracy. Since the lure tip made of hard plastics such as polycarbonate is press-fitted on the mouth portion of the syringe, it occasionally causes cracks in the skirt portion of the lure tip.

When performing injection with the conventional prefilled syringe having a capacity exceeding 20 ml, it is difficult with the hypodermic needle to pierce the skin covering a site to be injected since all of the lure tips of the prior art have to be constructed in a coaxial configuration with respect to the axis of the glass tube.

SUMMARY OF THE INVENTION

It is therefore an object of the present invention to provide a prefilled glass syringe which does not required a high precision-made glass body, which is easy in segregated disposal, and which is free from foreign matter entering into a medical solution.

According to the present invention the above and other objects are solved by providing a prefilled syringe comprising a syringe body of glass having at one end a reduced mouth portion and at the opposite end an opening, said syringe body being filled with a medical solution; a tip member liquid-tightly attached to said mouth portion of the syringe body; a sealing member arranged between said tip member and mouth portion to provide a liquid tight seal between them; a cap-shaped member for fixing said sealing member to the mouth portion; a covering means removably fitted on said tip member for covering the externally extending projection of said tip member; and a plunger means liquid-tightly fitted in said opening of the syringe body at a position close to the proximal end.

In the above structure, however, there is a fear of alteration or contamination of a medical solution contained therein due to removal of the covering member during storage since the covering means is removably fitted on the externally extending projection of the tip member.

According to the present invention, the above problems are solved by providing a prefilled syringe comprising:

- a syringe body of glass with a distal end formed into a configuration similar to that of a mouth portion of a vial;
- a sealing member with a through-hole extending in the axial direction of said syringe body, toward which the sealing member is fitted in the mouth portion of said syringe body;
- a tip member including a top wall, a skirt portion extending therefrom, and a tubular projection passing through said top wall, said skirt portion having at least one inwardly facing engaging projection and engaging means at lower parts of inner and outer walls thereof respectively and being provided with one or more slits extending in the axial direction thereof, said tubular projection including an outwardly extending projection and an inwardly extending projection, said outwardly extending projection extending from the top wall and being used for needle attachment, with said inwardly extending projection extending from the top wall and being fitted in the through-hole of said sealing member to lead a medical solution contained in said syringe body to said outwardly extending projection;
- a covering means for closing the outwardly extending projection of said tip member; and
- a holding member for holding said covering member along with said tip member in place on the mouth portion of said syringe body, said holding member including a top wall with an opening, and a skirt portion having an engaging projection engaged with the engaging means of said syringe body, said tip member being liquid-tightly fixed to the mouth portion of said syringe body by fitting said holding member on said tip member and then sliding it downward along the outer wall of said tip member, thereby permitting the skirt portion of said tip member to be bent inwardly so that the engaging projection of said tip member is engaged with the mouth portion of the syringe body.

In a preferred embodiment, the outwardly extending projection of the tip member is formed in an eccentric relationship with respect to the axis of the tip member.

The syringe body has at one end a mouth portion reduced in diameter and at the opposite end an opening for attachment of plunger means. The plunger means is fitted in the opening of the syringe body at a position close to the proximal end of the syringe body.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects and features of the present invention will become clear from the following description on preferred embodiments thereof with reference to the accompanying drawings throughout which like parts are designated by like reference numerals, and in which.

DETAILED DESCRIPTION OF THE PREFERRED EMBODIMENTS

Figure 1:
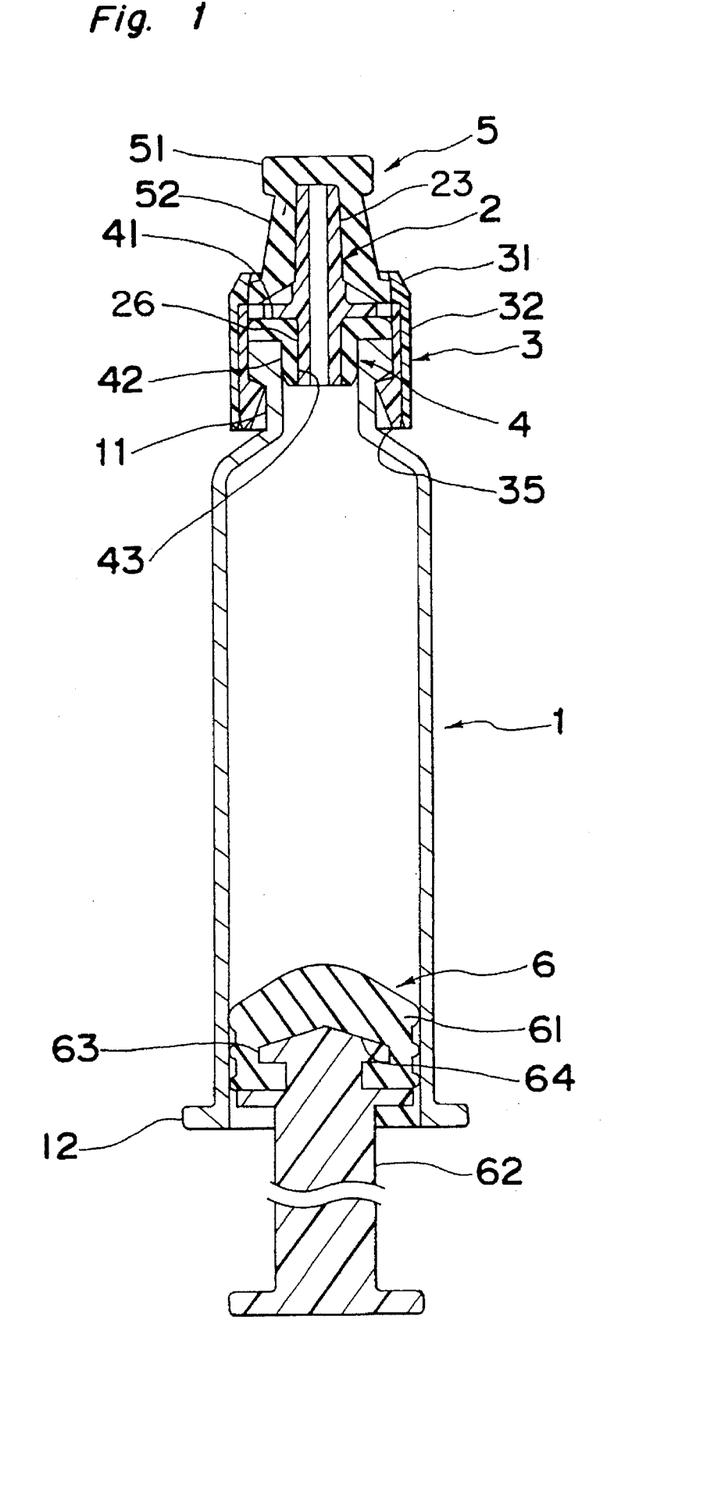
FIG. 1 is a cross section of a prefilled syringe according to one preferred embodiment of the present invention.

As shown in FIG. 1, a prefilled syringe of the present invention comprises a syringe body 1 made of glass, a tip member 2 liquid-tightly fixed to a distal end or mouth portion 11 of the syringe body 1, a sealing member or packing 4 for making a liquid tight seal between the tip member 2 and a mouth portion 11 of the syringe body 1, a covering member or a rubber cap 5 for closing an externally extending projection 23 of the tip member 2, and a holding member 3 for holding the tip member 2 in place on the mouth portion 11 of the syringe body 1 and for holding and fixing the rubber cap 5 to the tip member 2. The syringe body 1 is filled up with a medical solution (not illustrated in the drawings) and is closed at its proximal end by a plunger 6.

The syringe body 1 is a hollow glass tube having at one end the mouth portion 11 reduced in diameter and at the opposite end an opening for attachment of plunger means 6. The upper part 11 of the syringe body is formed like a mouth portion of a vial so as to have an annular projection which swells out and then continues straight up to the upper end. The syringe body 1 is provided with a flange 12 at the proximal end and closed by the plunger 6 fitted in the opening to close liquid-tightly.

The plunger 6 consists of a plunger rod 62 and a gasket 61 fitted on the top of the plunger rod 62 so as to move smoothly along the lumen of the syringe body 1. This gasket 61 is generally made of an elastic material such as natural rubber and synthetic rubber including butyl rubber, isoprene rubber and elastomers. The gasket 61 is formed into a short round body tapered toward the distal end, with a recess 64 for attachment of a head 63 of the plunger rod 62.

The packing 4 attached to the mouth portion 11 of the syringe body 1 includes a tubular body with a through-hole 43 and an upper flange 41 for making a liquid tight seal at contacting surfaces on the top surface of the mouth portion 11 and the packing 4, and a limb or leg portion 42 extending downward therefrom and in close contact with the inner wall of the mouth portion 11 for sealing up the mouth portion 11. An external diameter of the leg portion 42 is almost equal to an internal diameter of mouth portion 11, while the diameter of the through-hole 43 is slightly smaller than the external diameter of the outlet portion 26 of the tip member 2. The packing 4 is usually made of the same elastic material as that used for the gasket 61. A ring-shaped packing P with the same internal diameter as that of the mouth portion 11, as shown in FIG. 10, may be used as a sealing member instead of the packing 4.

The tip member 2 is attached to the mouth portion 11 through the packing 4. The tip member 2 is, usually of a flexible material such as polypropylene, polyethylene, polycarbonate, ABS resin and the like. The tip member 2 is slidable along the outer wall of the mouth portion 11 of the syringe body 1 when constructing the prefilled syringe.

Figure 3:
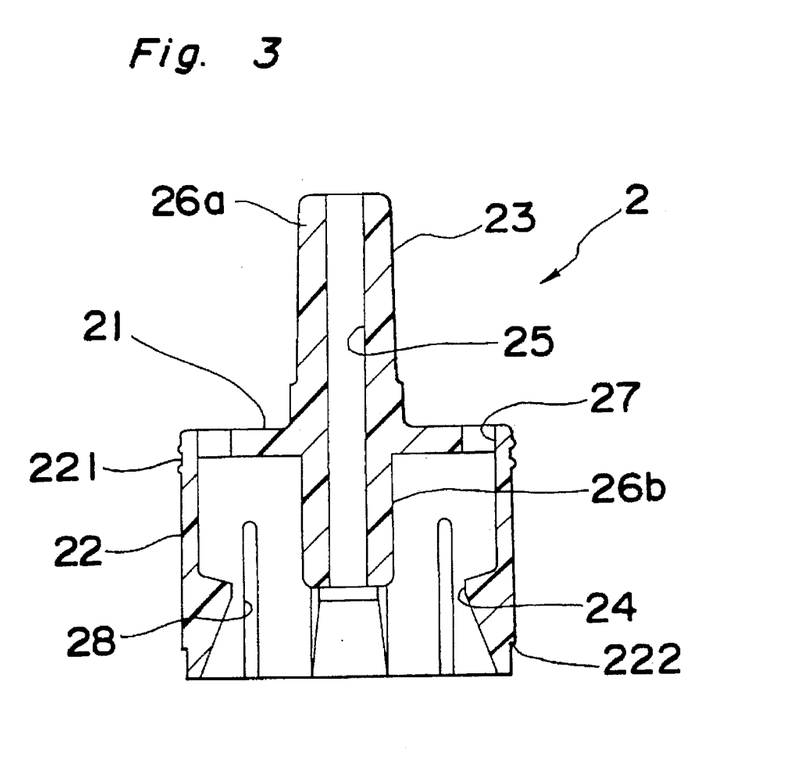
FIG. 3 is a cross section of a tip member shown in FIG. 2.

As best shown in FIG. 3, the tip member 2 is molded into a cap-like member including a top wall 21, a tubular projection 23 passing through the top wall 21, and a skirt portion 22 slightly swelling out to the bottom. The tubular projection 23 is divided, by the top wall 21, into two portions, i.e., an outwardly extending portion 26a which extends upward from the top wall 21, and an inwardly extending portion 26b which extends downward from the top wall 21. The outwardly extending portion 26a is used for attachment of a needle in use, while inwardly extending portion 26b is fitted in the packing 4 for leading a medical solution in the syringe body 1 to the outwardly extending portion 26a. To this end, the tubular projection 23 is provided with a passage 25 passing through the lower and upper portions 26a and 26b. Thus, a medical solution in the syringe can be pushed out therefrom through the needle attached to the upper portion 26a of the tip member 2.

Figure 2:
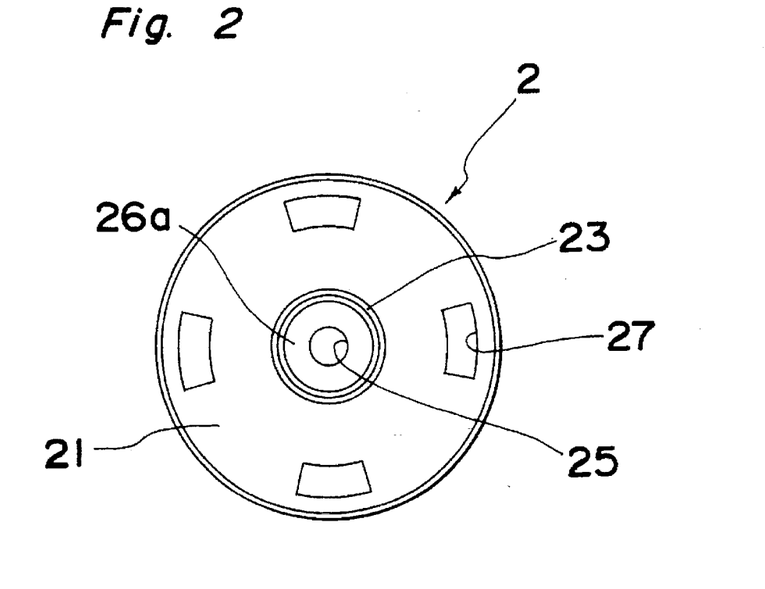
FIG. 2 is a plan view of a tip member used in the prefilled syringe shown in FIG. 1.
Figure 4:
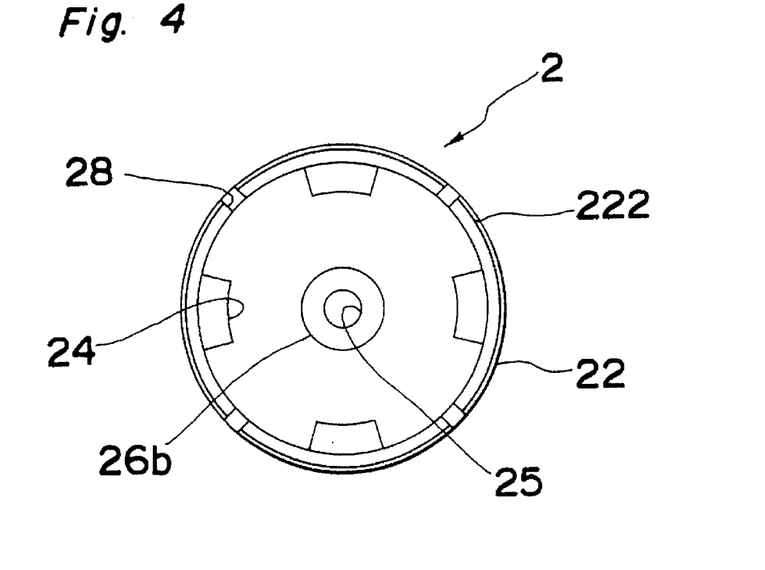
FIG. 4 is a bottom view of a tip member shown in FIG. 2.

The skirt portion 22 is provided at a lower part of the inner wall with engaging projections 24 (four projections in the figures of the drawings) and at a lower part of the outer wall with engaging means 222 which engage with an engaging projection 35 of the holding member 3. The skirt portion 22 is provided with one or more slits 28 extending axially from the bottom end of the skirt so as to be expandable at its lower part. Preferably, three or four slits 28 are made in the skirt portion.

Figure 9:
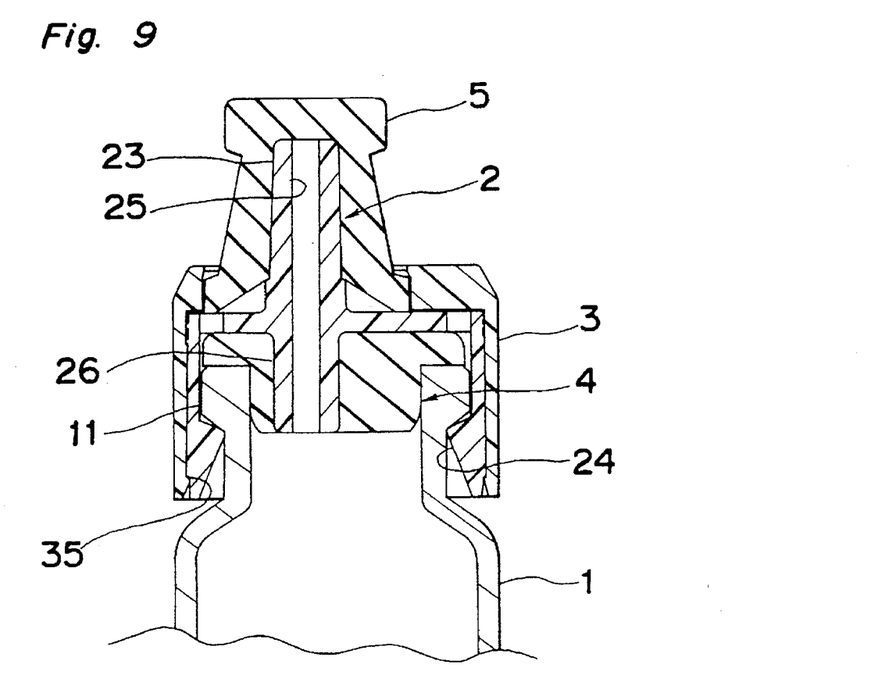
FIG. 9 is a cross section illustrating an essential part of another embodiment of the present invention.

The upper part of the tubular projection, i.e., outwardly extending portion 26a for needle attachment, has an outer wall usually reduced in diameter toward the top, which is closed by the sealing member or rubber cap 5. If the syringe has a large capacity, as shown in FIG. 9, the tubular projection 23 may be formed in an eccentric position with respect to the axis of the tip member 2 to facilitate insertion of a needle into the patient's skin.

The engaging projections 24 on the lower part of the interior wall of the skirt 22 are engaged with an annular lip formed on the neck portion of the syringe body 1 when the tip member 2 has snapped over the annular lip after being moved smoothly along the outer wall of the annular lip of the syringe 1. The engaging means 222 on the lower part of the outer wall of the skirt 22 is constructed to engage with the engaging projection 35 of the holding member 3.

If necessary, the top wall 21 may be provided with bores 27 for removal of the tip member 2 from a mold after molding. Also, the tip member 2 may be provided at an upper part of the skirt 22 with an annular groove 221 which engages with engaging projection 35 of the holding member 3 mentioned later. With the tip member 2 having the annular groove 221, it is possible to keep the holding member 3 on the tip member 2. Thus, it is possible to attach the tip member 2, holding member 3 and packing 4 to the mouth portion 11 of the syringe body 1 at one time, provided that tip member 2, holding member 3, packing 4 and rubber cap 5 are assembled into one piece.

The holding member 3 is fitted on the tubular projection 23 of the tip member 2 provided with the or rubber cap 5, so that tip member 2 is fixed to the mouth portion 11 of the syringe body 1 and the rubber cap 5 is fixed to the tip member 2.

Figure 5:
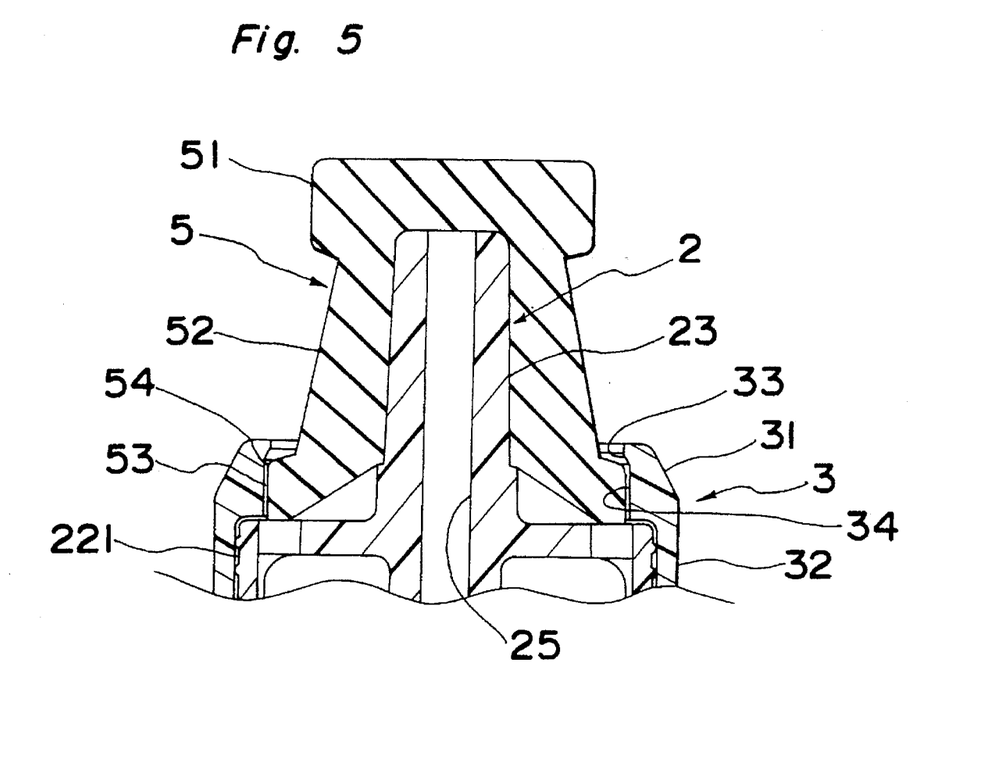
FIG. 5 is an enlarged cross section of a distal portion of the prefilled syringe of FIG. 1, illustrating the relationship between a sealing member and a holding member.

The rubber cap 5 is one example of the covering means to be attached to the tubular projection 23 of the tip member 2. As shown in FIG. 5, the rubber cap 5, usually of the same elastic material as that of the sealing member or packing, 4 is composed of a top wall 51 and a downwardly enlarged skirt 52. At the bottom of the skirt 52 there is an annular projection 53 adapted to be pressed against the tip member 2 by the holding member 3. The annular projection 53 may include a rounded upper corner portion 54 so as to facilitate removal of the rubber cap 5.

The holding member 3 is made of a synthetic resin similar to that of the tip member 2 and composed of a top wall 31 and a skirt 32. The top wall 31 is provided with an opening 34 having an inwardly facing annular rim 33 which contacts with the annular projection 53 of the rubber cap 5 and presses it against the top wall 21 of the tip member 2. When sliding the holding member 3 along the outer wall of the skirt 22 of the tip member 2, the skirt 22 (which is downwardly enlarged in diameter) is flexed inwardly so that the engaging projections 24 is engaged with the mouth portion 11 of the syringe body 1.

On the other hand, the engaging projection 35 of the holding member 3 is engaged with the engaging means 222, e.g., an undercut, formed in the lower part of the outer wall of the tip member 2 when the inner surface of the top wall 31 of the holding member 3 comes into contact with the upper surface of the top wall 21 of the tip member 2.

Figure 7:
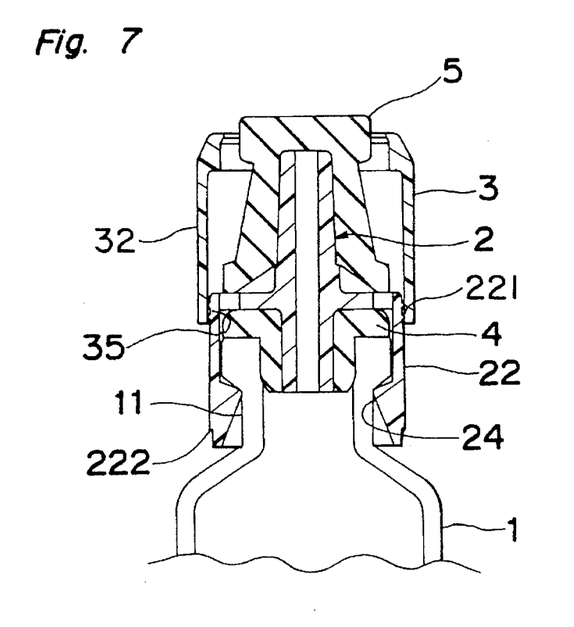
Figure 8:
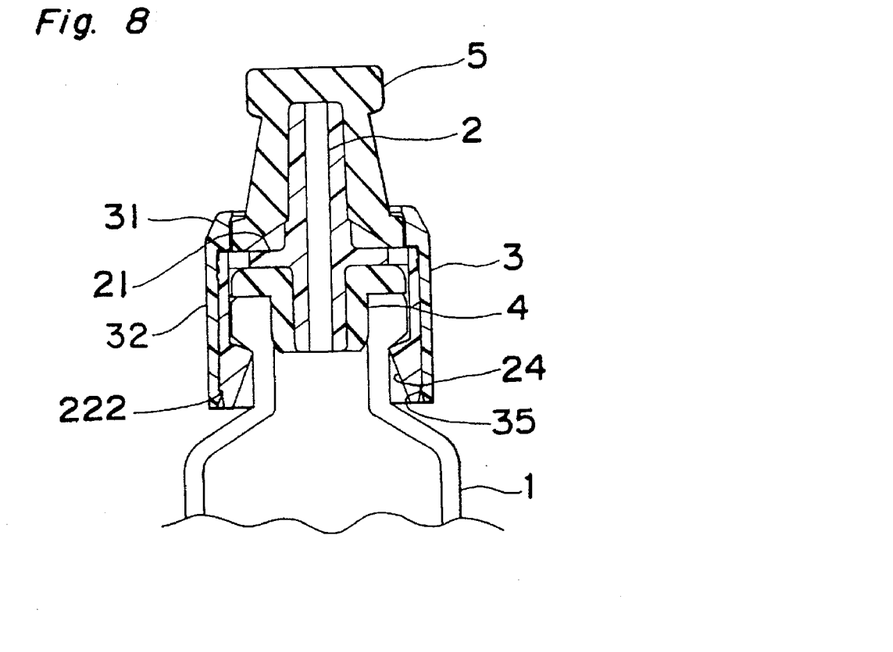

The assembling of the pre-filled syringe of the present invention will be explained below, making reference with FIGS. 6 to 8.

Figure 6:
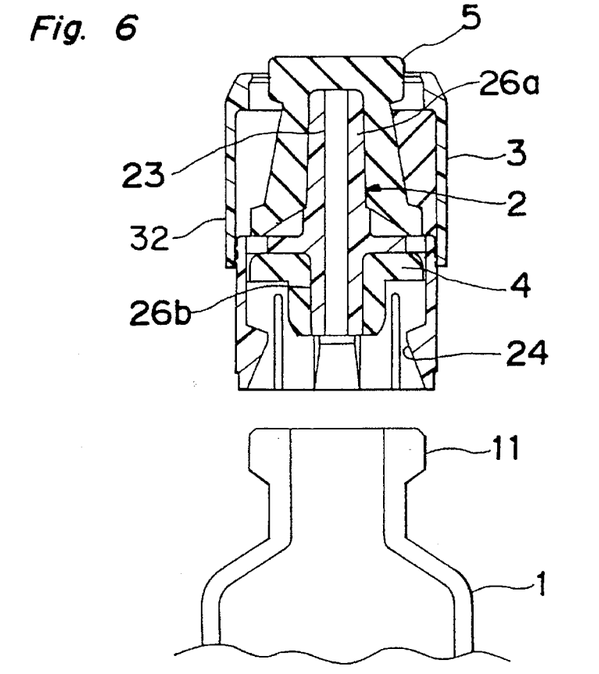
FIGS. 6–8 show an assembly process for attachment of a tip member to the syringe body.

As shown in FIG. 6, the packing 4 is first fitted on the inwardly extending tubular portion 26b of the tip member 2, and the rubber cap 5 is fitted on the outwardly extending tubular portion 26a. Then, the holding member 3 is put on the rubber cap 5 so that the lower part of its skirt 32 is engaged with the groove 221 of the tip member 2. The assembled sealing means is put on the mouth portion 11 of the syringe body 1 and pushed down, whereby the tip member 2 is moved downward along the mouth portion 11 of the syringe 1 and stopped at a position as shown in FIG. 7. At the same time, the packing 4 is fitted in the mouth portion 11 of the syringe body 1. The holding member 3 is moved downward to a position where the inner surface of the top wall 31 of the holding member 3 comes into contact with the top wall 21 of the tip member 2. At the same time, the engaging projection 35 of the holding member 3 is engaged with the engaging means 222 provided in the lower portion of the tip member 2, whereby the holding member 2 is fixed to the mouth portion 11 of the syringe body 1.

As will be understood from the above, the prefilled syringe of the present invention may be so constructed that the tip member of a synthetic resin is attached to the mouth portion of the syringe body by first fitting the packing in the mouth portion of the syringe, fitting the inwardly extending projection of the tip member in the through-hole of the packing, fitting the rubber cap on the outwardly extending projection of the tip member, mounting the holding member on the rubber cap and then sliding the holding member along the skirt portion of the tip member to fix the tip member to the mouth portion of the syringe body. Accordingly, the prefilled syringe of the present invention has the following advantages:

(1) It is possible to provide prefilled syringes employing a glass syringe body at a low price since the syringe body of glass does not require close tolerance accuracy as compared with that of the prior art, since it requires a small number of parts, and since it is easy to construct and suitable for mass-production;

(2) It is possible to produce prefilled syringes of a large capacity employing a syringe made of glass, since the outwardly extending projection for needle attachment can be formed in an eccentric position with respect to the axis of the syringe body;

(3) It can be applied to prefilled syringes of a large capacity employing a syringe body made of glass since the configuration of the outwardly extending projection for needle attachment may be selected according to the demand;

(4) It is possible to protect the medical solution from alteration or contamination due to removal of the rubber cap during storage; and (5) It requires no segregated disposal since no metal member is used for the individual parts.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A syringe tip assembly for attachment to a mouth portion of a syringe body, said syringe tip assembly comprising:

a sealing member insertable into the mouth portion of said syringe body, said sealing member including a through-hole extending therethrough;

a tip member including a top wall, a skirt portion extending therefrom, and a tubular projection passing through said top wall, said skirt portion having at least one inwardly facing engaging projection and engaging means thereon, said tubular projection including an outwardly extending projection and an inwardly extending projection, said outwardly extending projection extending from the top wall for attachment of a needle thereto, said inwardly extending projection extending from the top wall and fitted in the through-hole of said sealing member;

covering means for closing the outwardly extending projection of said tubular projection; and a holding member for holding said covering means and said tip member in place on the mouth portion of said syringe body, said holding member including a top wall member and a skirt member, said skirt member having an engaging projection thereon engagable with the engaging means of the skirt portion of said tip member.

2. The syringe tip assembly according to claim 1, wherein the outwardly extending projection of the tubular projection is formed in an eccentric relationship with respect to a central longitudinal axis of the tip member.

3. The syringe tip assembly according to claim 1, wherein the skirt portion includes inner and outer walls, and wherein the at least one engaging projection and the engaging means are located at a lower end of said inner and outer walls, respectively.

4. The syringe tip assembly according to claim 1, wherein the skirt portion includes at least one slit therein extending in a longitudinal direction thereof.

5. The syringe tip assembly according to claim 1, wherein the covering means includes a resilient cap having a top wall and a outwardly tapering skirt portion extending therefrom.

6. The syringe tip assembly according to claim 5, wherein the top wall member of the holding member includes an aperture, and wherein said outwardly tapering skirt portion of said covering means extends through said aperture when in an assembled position.

7. The syringe tip assembly according to claim 6, wherein the covering means further includes an annular projection spaced from said top wall, said outwardly tapering skirt portion extending between said top wall and said annular projection.

8. The syringe tip assembly according to claim 7, wherein the top wall member of the holding member is engagable with the annular projection of the covering means when in said assembled position.

9. The syringe tip assembly according to claim 8, wherein the skirt portion includes inner and outer walls, and wherein the at least one engaging projection and the engaging means are located at a lower end of said inner and outer walls, respectively.

10. The syringe tip assembly according to claim 9, wherein the outwardly extending projection of the tubular projection is formed in an eccentric relationship with respect to a central longitudinal axis of the tip member.

11. The syringe tip assembly according to claim 10, wherein the skirt portion includes at least one slit therein extending in a longitudinal direction thereof.

12. The syringe tip assembly according to claim 11, and including a syringe body attached to said tip member.

13. The syringe tip assembly according to claim 5, wherein the covering means further includes an annular projection spaced from said top wall, said outwardly tapering skirt portion extending between said top wall and said annular projection.

14. The syringe tip assembly according to claim 13, wherein the top wall member of the holding member is engagable with the annular projection of the covering means when in an assembled position.

15. The syringe tip assembly according to claim 1, and including a syringe body attached to said tip member.

16. A prefilled syringe comprising:
a syringe body of glass, said syringe body including a distal end formed into a mouth portion;
a sealing member, said sealing member including a through-hole extending in the axial direction of said syringe body toward which the sealing member is fitted in the mouth portion of said syringe body;
a tip member including a top wall, a skirt portion extending therefrom, and a tubular projection passing through said top wall, said skirt portion having inner and outer walls, said skirt portion further having at least one inwardly facing engaging projection and engaging means at lower parts of said inner and outer walls, respectively, said skirt portion further having one or more slits extending in the axial direction thereof, said tubular projection including an outwardly extending projection and an inwardly extending projection, said outwardly extending projection extending from the top wall and being used for needle attachment, said inwardly extending projection extending from the top wall and being fitted in the through-hole of said sealing member to lead a medical solution contained in said syringe body to said outwardly extending projection;
covering means for closing the outwardly extending projection of said tip member; and
a holding member for holding said covering means along with said tip member in place on the mouth portion of said syringe body, said holding member including a top wall, said top wall of said holding member including an opening therein, said holding member further including a skirt portion having an engaging projection engaged with the engaging means of said tip member, said tip member being liquid-tightly fixed to the mouth portion of said syringe body by fitting said holding member on said tip member and then sliding it downwardly along with outer wall of said tip member, thereby permitting the skirt portion of said tip member to be bent inwardly so that the engaging projection of said tip member is engaged with the mouth portion of the syringe body;
wherein the outwardly extending projection of the tip member is formed in an eccentric relationship with respect to the axis of the tip member.

17. The prefilled syringe according to claim 16, wherein the covering means includes a resilient cap having a top wall and a outwardly tapering skirt portion extending therefrom.

18. The prefilled syringe according to claim 17, wherein said outwardly tapering skirt portion of said covering means extends through said opening in the top wall of the holding member when in an assembled position.

19. The prefilled syringe according to claim 17, wherein the covering means further includes an annular projection spaced from said top wall, said outwardly tapering skirt portion extending between said top wall and said annular projection.

20. The prefilled syringe according to claim 19, wherein the top wall member of the holding member is engagable with the annular projection of the covering means when in an assembled position.

* * * * *